United States Patent

Albayrak et al.

[11] Patent Number: 6,106,807
[45] Date of Patent: Aug. 22, 2000

[54] USE OF METHYLENEMALONDIESTER DERIVATIVES FOR THE PRODUCTION OF GAS-CONTAINING MICROPARTICLES FOR ULTRASOUND DIAGNOSIS, AS WELL AS MEDIA THAT CONTAIN SAID PARTICLES

[75] Inventors: Celal Albayrak; Georg Rössling, both of Berlin, Germany

[73] Assignee: Schering Aktiengesellschaft, Germany

[21] Appl. No.: 08/894,593

[22] PCT Filed: Feb. 9, 1996

[86] PCT No.: PCT/EP96/00538

§ 371 Date: Feb. 23, 1998

§ 102(e) Date: Feb. 23, 1998

[87] PCT Pub. No.: WO96/25954

PCT Pub. Date: Aug. 29, 1996

[30] Foreign Application Priority Data

Feb. 23, 1995 [DE] Germany ............. 195 08 049

[51] Int. Cl.[7] ................ A61B 8/00; A61K 9/50
[52] U.S. Cl. .......... 424/9.52; 424/497; 424/501; 252/302
[58] Field of Search ............ 424/9.52, 9.51, 424/9.5, 489, 490, 497, 501; 560/82; 252/302; 427/213.3

[56] References Cited

U.S. PATENT DOCUMENTS 5,425,366   6/1995   Reinhardt et al. ............. 128/662.02

FOREIGN PATENT DOCUMENTS

93/25242   12/1993   WIPO ............. A61K 49/00

OTHER PUBLICATIONS

Keyser et al., "Poly (dialkyl methylidenemalonate) Nanoparticles as a Potential Drug Carrier" Journal of Pharmaceutical Sciences, vol. 80, No. 1, pp. 67–70, Jan. 1991.

Breton, P. et al., "New Poly(methylidene Malonate Nanoparticles" NATO ASI Ser., Ser. A, pp. 161–172, 1994.

*Primary Examiner*—S. Mark Clardy
*Assistant Examiner*—Michael G. Hartley
*Attorney, Agent, or Firm*—Millen, White, Zelano & Branigan, P.C.

[57] ABSTRACT

The invention relates to the use of methylenemalondiester derivatives of general formula I

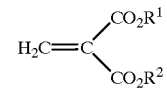

in which $R^1$ and $R^2$ have different meanings, for the production of gas-containing particles for ultrasonic diagnosis, as well as ultrasonic contrast media that contain these particles.

16 Claims, No Drawings

USE OF METHYLENEMALONDIESTER DERIVATIVES FOR THE PRODUCTION OF GAS-CONTAINING MICROPARTICLES FOR ULTRASOUND DIAGNOSIS, AS WELL AS MEDIA THAT CONTAIN SAID PARTICLES

This application is a 371 of PCT/EP96/00538, filed Feb. 9, 1996.

The invention relates to the object that is characterized in the claims, i.e., the use of asymmetrical or symmetrical methylenemalondiester derivatives for the production of gas-containing microparticles, as well as the contrast media that contain these particles, for ultrasound diagnosis.

In medicine, ultrasound diagnosis has been very widely used because of its straightforward, simple handling. Ultrasonic waves are reflected at the interfaces of different types of tissue. The echo signals that are produced in this process are electronically enhanced and made visible. The visualization of blood vessels and internal organs using ultrasound generally does not allow the visualization of the blood flow that is present in it. Liquids, especially blood, provide ultrasonic contrast only when differences in density and compressibility exist compared to the surrounding area. As contrast media, e.g., substances that contain gases or that produce gases are used in medical ultrasound diagnosis since the impedance difference between the gas and the surrounding blood is considerably greater than that between liquids or solids and blood (Levine, R. A., J. Am. Coll. Cardiol. 3: 28, 1989; Machi I. J. CU 11:3, 1983).

It is known that peripheral injections of solutions that contain fine gas bubbles can ensure cardiac echo contrasts (Roelandt, J., Ultrasound Med. Biol. 8: 471–492, 1982). These gas bubbles are obtained in physiologically compatible solutions by, e.g., shaking, other agitation, or the addition of carbon dioxide. These gas bubbles are not standardized with respect to number or size, however, and can be produced only in an inadequate manner. They also are not generally stabilized, so that their service life is short. Their average diameters in most cases exceed that of an erythrocyte, so that passage through the lung capillaries, with subsequent contrasting of organs such as the left side of the heart, liver, kidney or spleen, is not possible.

Moreover, such bubbles are not suitable for quantification since the ultrasonic echoes that they produce consist of several processes that cannot be separated from one another, such as bubble production, coalescence, and dissolution. Thus, for example, it is not possible to obtain information on transit times with the aid of these ultrasonic contrast media by measuring the plot of the contrast in the myocardium. For this purpose, contrast media are needed whose scatter elements exhibit sufficient stability.

EP 0 131 540 describes the stabilization of gas bubbles using sugar. Thus, the reproducibility and homogeneity of the contrast effect are improved, but these bubbles do not survive passing through the lungs.

EP 0 122 624 and 0 123 235 describe that the gas bubble-stabilizing effect of sugars, sugar alcohols and salts is improved by the addition of surface-active substances. The ability to pass through the lung capillaries and the possibility of visualizing the arterial femoral blood vessels as well as various organs such as the liver or spleen are provided with these ultrasonic contrast media. In this connection, however, the contrast effect is limited to the vascular lumen since the bubbles are not taken up by the tissue cells.

None of the ultrasonic contrast media described remains unaltered in the body for a prolonged time. Organ visualization with sufficient signal intensity by selective concentration after i.v. administration or quantification is not possible with these media.

Encapsulation of gases such as, for example, air as an ultrasonic contrast medium is described in EP 0 224 934. The wall material that is used in this connection consists of protein, especially human serum albumin with the known allergenic properties; denaturing may also add cytotoxic effects.

Gas-containing microparticles for ultrasound diagnosis based on biodegradable, synthetic materials are described in EP 0 327 490 and EP 0 458 745. These media have a sufficient in-vivo service life and accumulate intravenous administration intracellularly in the reticuloendothelial system and thus also in the liver or spleen.

The object of this invention was to provide contrast media for ultrasound diagnosis, which overcome the drawbacks of the prior art, i.e., to develop ultrasonic contrast media based on microparticles, which provide a clear contrast to surrounding tissue, are small and stable, such that they reach the left half of the heart after intravenous administration without significant loss of gas and in a basically quantitative manner, exhibit good compatibility and do not have any allergenic potential, do not agglomerate with one another in water or blood and can be produced quickly and simply.

This object is achieved by this invention.

It has been found that gas-filled particles that consist of polymerized asymmetrical or symmetrical methylenemalonesters of general formula I

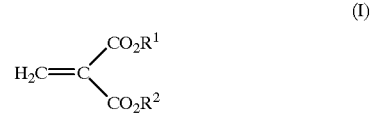

in which radicals $R^1$ and $R^2$ can be the same or different and mean saturated or unsaturated groups that contain 1 to 8 carbon atoms, which optionally contain oxygen atoms (ether groups) and carboxyl groups (esters), are extremely well suited as contrast media for ultrasonic diagnosis.

As radicals $R^1$ and $R^2$, we can mention by way of example $CH_3$, $C_2H_5$, n-$C_3H_7$, iso-$C_3H_7$, n-$C_4H_9$, iso-$C_4H_9$, n-$C_5H_{11}$, n-$C_6H_{13}$, $CH_2CO_2C_2H_5$, $CH_2$—CH=$CH_2$, $CH_2$—C≡CH, $CH_2$—O—$CH_3$, $C_2H_4OC_2H_5$, $CH_2CO_2C_2H_5$, $CH_2CH_2CH_2CO_2C_2H_5$ and the allyl group, whereby $R_1$ and $R_2$, independently of one another, can be the same or different.

Preferably,

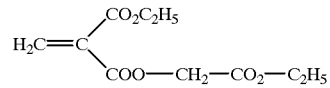

is used as a methylenemalonester.

Air, nitrogen, oxygen, noble gases, carbon dioxide, and fluorocarbons are suitable as gases that are contained in particles.

The particles have an average size in the range of 500 nm to 7 μm.

Corresponding media especially have the advantage that the latter can be catabolized more quickly in vivo and the degradation products are toxicologically harmless.

Since wall thickness can be influenced by the production processes, particles can be produced whose vibration modes can be stimulated by the sound field, thus adding an additional component to contrasting.

Another aspect of the invention relates to a process for the production of particles according to the invention.

The production of particles according to the invention based on asymmetrical or symmetrical methylenemalonesters is carried out by the monomeric methylenemalonesters that are desired in each case being dispersed by a stirrer in an aqueous gas-saturated buffer solution, which optionally contains one or more surface-active substance(s); after polymerization is completed (about 2–6 hours), the particles that are obtained are separated, optionally washed with water, and then taken up in a pharmaceutically acceptable suspension medium and freeze-dried.

As surface-active substances that are optionally fed to the reaction process, preferably substances from the group of Poloxamers(R), polysaccharides, polysorbates, saccharose mono- or di-esters, polyethylene glycol alkyl ethers, as well as mixtures of them, are suitable.

The pH of the aqueous gas-saturated buffer solution is preferably between 5 and 8. The separation of the particles is carried out using flotation.

The separated particles are then optionally washed, resuspended in a suspension medium, and freeze-dried. As a suspension medium, water for injection purposes is suitable, optionally with an addition of common salt and/or glucose and/or mannitol and/or lactose, which optionally additionally contains a surface-active substance, such as, e.g., polysaccharides, polysorbates, Poloxamers(R), saccharose mono- or diester- or polyethylene glycol alkyl ethers or mixtures thereof.

The production of the ready-for-use, injectable ultrasonic contrast media from the freeze-dried particles is done by resuspending the lyophilizate in a pharmaceutically acceptable suspension medium such as, e.g., water, p.i., aqueous solutions of one or more inorganic salts such as physiological electrolyte solutions and buffer solutions, such as, e.g., tyrodes, aqueous solutions of mono- or disaccharides such as glucose or lactose, sugar alcohols such as mannitol, which optionally in addition also contain a surface-active substance, e.g., from the group of polysorbates or polysaccharides or polyvinylpyrrolidines or polyethyleneglycolyl ethers, saccharose mono- and diesters or substances from the group of Poloxamers(R) or mixtures thereof and/or a physiologically compatible multivalent alcohol such as glycerol. Water that is suitable for injection purposes is a preferred suspension medium. The total concentration of the optionally dissolved substances is 0–15% by weight.

An alternative process for the production of ready-to-use, injectable preparations consists in the fact that in a process according to the invention—for the production of particles—the final freeze-drying is omitted.

To increase the safety of administration, filtering of the suspension can be performed immediately before injection.

The following examples are used for a more detailed explanation of the object of the invention, without intending that it be limited to these examples.

The production of the methylenemalonester derivatives that are used as starting compounds is known in the literature and is described in, for example, DE-PS 27 34 082; US-PS 4,931,584, J. Org. Chem. 48, 3603 (1983) as well as in Makromoleculare Chemie [Macromolecular Chemistry] 107, 4–5 (1967).

EXAMPLE 1

1 ml of diethylmethylidenemalonate is dispersed with a stirrer (Dispermat-FT, VMA-Getzmann GmbH) in 100 ml of 0.01 m phosphate buffer with a pH of 7.4, which contains 1% dextran-8 (Serva, Feinbiochemica GmbH & Co.) at 20° C. for 60 minutes at 10,000 rpm. Then, the reaction mixture is transferred into a flask that is equipped with a stirrer and is polymerized for another 6 hours at room temperature while being stirred (300 rpm).

The ultrasound-active, gas-filled nano- or microparticles are separated by flotation, washed several times with water or 0.9% NaCl solution, and taken up in 200 ml of an aqueous solution of 1% dextran-8. The particles have an average size of 800 nm and show excellent ultrasound activities. Thus, the backscatter coefficient $\alpha_s=7.8\times10^{-2}$ dB/cm that is found in an in-vitro test is approximately 5 mHz, $C=2.2\ 10^{-7}$ T/ml.

EXAMPLE 2

The procedure is as in Example (1), whereby the buffer system has a pH of 8.0 and dextren-8 is replaced by dextran-10. The particles have an average size of 700 nm.

The particles are taken up in 150 ml of a 5% mannitol solution that contains 0.1% dextran.

EXAMPLE 3

The procedure is as in Example (1), whereby the buffer system has a pH of 7.4, and dextren-8 is replaced by polyvinylpyrrolidone Kollidon(R) PF-17. The particles have an average size of 1.3 μm. The particles are taken up in 150 ml of a 5% glucose solution that contains 0.1% Kollidon(R) PF-17.

EXAMPLE 4

The procedure is as in Example (1), whereby dextran-8 is replaced by Brij(R)-35. The particles have an average size of 2.0 μm The particles are taken up in 150 ml of a 0.5% glucose solution that contains 1% Brij(R)-35.

EXAMPLE 5

The procedure is as in Example (1), whereby dextran-8 is replaced by Brij(R)-96. The particles have an average size of 2.0 μm.

The particles are taken up in 150 ml of a 0.1% Brij(R)-96 solution.

EXAMPLE 6

The procedure is as in Example (1), whereby dextran-8 is by 2% Tween(R)-20.

The particles are taken up in 150 ml of a 5% mannitol solution that contains 0.1% Tween(R)-20. The particles have an average size of 1.0 μm.

EXAMPLE 7

1 ml of monomer "1-ethoxycarbonyl, 1-ethoxycarbonylmethylene oxycarbonylethane" is dispersed with a stirrer (Disperment FT, Getzmann GmbH) in 100 ml of aqueous phosphate buffer ($KH_2PO_4/Na_2HPO_4$, 0.066 N, pH 5.5), which contains 1% dextran-8 (Serva, Feinbiochemica GmbH & Co.) at 20° C. for 60 minutes at 8000 rpm. Then, the reaction mixture is transferred into a flask that is equipped with a stirrer and polymerized for another 6 hours at room temperature while being stirred (300 rpm). The ultrasound-active or gas-filled nano- or microparticles or particles are separated either by flotation or centrifuging, washed with water several times, and taken up in 200 ml of a 5% mannitol solution that contains 0.1% of dextran-8.

The particles have an average size of 1.5 μm and show excellent ultrasound activities. In an in-vitro experiment, a backscatter coefficient of $\alpha_s=1.5\times10^{-1}$ dB/cm at 5 mHz, C=1.0 $10^{-7}$ T/ml was measured.

EXAMPLE 8

The procedure is as in Example (7), whereby the phosphate buffer has a pH of 6.0. The particles have an average size of 1.0 μm.

EXAMPLE 9

The procedure is as in Example (7), whereby the phosphate buffer has a pH of 6.5. The particles have an average size of 1.2 μm.

EXAMPLE 10

The procedure is as in Example (7), whereby the phosphate buffer is replaced by citric acid (0.1 m)/Na$_2$HPO$_4$ (0.2 m) buffer, pH 5.5. The particles have an average size of 1.0 μm.

EXAMPLE 11

The procedure is as in Example (7), whereby dextran-8 is replaced by dextran-10. The particles have an average size of 0.8 μm. The particles are taken up in 200 ml of a 5% glucose solution that contains 5% dextran-10.

EXAMPLE 12

The procedure is as in Example (7), whereby dextran-8 is replaced by 3% polyvinylpyrrolidone PF-17. The particles exhibit an average size of 1.5 μm. The particles are taken up in 200 ml of a 5% mannitol solution that contains 0.5% Kollidon$^{(R)}$ PF-17.

EXAMPLE 13

The procedure is as in Example (7), whereby dextran-8 is replaced by 3% Tween$^{(R)}$-80. The particles have an average size of 1.2 μm. The particles are taken up in 200 ml of a 5% glucose solution.

EXAMPLE 14

The procedure is as in Example (7), whereby dextran-8 is replaced by 2% Tween$^{(R)}$-40. The particles have an average size of 1.0 μm. These particles are taken up in 150 ml of a 5% mannitol solution.

EXAMPLE 15

The procedure is as in Example (7), whereby dextran-8 is replaced by 3% Pluronic$^{(R)}$ F 68. The particles have an average size of 1.8 μm. The particles are taken up in 150 ml of a 5% mannitol solution.

What is claimed is:

1. Gas-filled microparticles which comprise a wall material of polymerized methylenemalonesters of formula I:

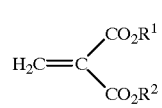

wherein radicals R$^1$ and R$^2$, being the same or different, are saturated or unsaturated groups of 1–8 carbon atoms optionally containing ether oxygen atoms and/or ester carboxyl groups and a gas contained within said wall material.

2. The microparticles of claim 1, wherein radicals R$^1$ and R$^2$, being the same or different, are methyl, ethyl, isopropyl, propyl, butyl, pentyl, allyl, propinyl, methoxymethyl, ethoxyethyl, ethoxycarbonylmethyl or ethoxycarbonylpropyl groups.

3. The microparticles of claim 1, wherein radical R$^1$ is ethyl and radical R$^2$ is ethoxycarbonylmethyl.

4. The microparticles of claim 1, wherein the gas is air, nitrogen, oxygen, a noble gas, carbon dioxide, a fluorocarbon gas or a mixture thereof.

5. The microparticles of claim 1, which have an average size of from 500 nm to 7 μm.

6. The microparticles of claim 1 in freeze-dried form.

7. A medium for contrast enhancement in ultrasound diagnosis which comprises the microparticles of claim 1 in a pharmaceutically acceptable suspension medium.

8. The medium of claim 7, wherein the pharmaceutically acceptable suspension medium is water, p.i., an aqueous solution of one or more inorganic salts or an aqueous solution of one or more mono- or di-saccharides or sugar alcohols.

9. The medium of claim 7, wherein the pharmaceutically acceptable suspension medium contains a surface-active substance.

10. The medium of claim 9, wherein the surface-active substance is a polysorbate, polysaccharide, polyvinylpyrrolidone, polyethyleneglycol ether, saccharose mono- or di-ester, a poloxamer or mixture thereof.

11. The medium of claim 7, wherein the pharmaceutically acceptable suspension medium contains a multivalent alcohol.

12. A method for ultrasound diagnosis which comprises administering to a patient a contrast enhancement effective amount of a medium according to claim 7 and performing the ultrasound diagnosis.

13. A method for preparing the microparticles of claim 1, which comprises polymerizing at least one methylenemalonateester of formula I in a stirred aqueous gas-saturated buffer solution, optionally containing one or more surface-active substances, and separating gas filled microparticles resulting therefrom.

14. The method of claim 13, further comprising taking up the gas filled microparticles in a pharmaceutically acceptable suspension medium optionally after being washed with water.

15. The method of claim 13, further comprising freeze-drying the gas filled microparticles.

16. The method of claim 14, further comprising freeze-drying the gas filled microparticles after they are taken up in a pharmaceutically acceptable suspension medium.

* * * * *